(12) United States Patent
Hench

(10) Patent No.: US 7,602,509 B1
(45) Date of Patent: Oct. 13, 2009

(54) METHOD FOR SELECTING OPTICAL CONFIGURATION FOR HIGH-PRECISION SCATTEROMETRIC MEASUREMENT

(75) Inventor: John J. Hench, Los Gatos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 0 days.

(21) Appl. No.: 12/077,335

(22) Filed: Mar. 18, 2008

(51) Int. Cl.
*G01B 11/14* (2006.01)
(52) U.S. Cl. .................................. 356/625; 356/445
(58) Field of Classification Search .............. 356/445, 356/601, 625
See application file for complete search history.

(56) References Cited

U.S. PATENT DOCUMENTS

| | | | |
|---|---|---|---|
| 7,333,200 B2 | 2/2008 | Sezginer et al. | |
| 7,375,831 B2 * | 5/2008 | Tanaka et al. | 356/636 |
| 7,385,699 B2 | 6/2008 | Mieher et al. | |
| 2008/0084567 A1 | 4/2008 | Fabrikant et al. | |

* cited by examiner

*Primary Examiner*—Roy Punnoose
(74) *Attorney, Agent, or Firm*—Okamoto & Benedicto LLP

(57) ABSTRACT

The present application discloses a method for selecting an optical configuration for a high-precision scatterometric measurement. A geometric parameterization of a grating is determined, wherein the grating comprises a periodic structure. The geometric parameterization is used to generate a representative set of model structures. An eigenvalue method is utilized to compute, for each model structure, a set of solutions which satisfy a Rayleigh condition within the grating. The Raleigh condition within the grating is satisfied when a vertical component of a propagating mode within the grating is zero. Other embodiments, features and aspects are also disclosed herein.

24 Claims, 5 Drawing Sheets

METHOD FOR SELECTING OPTICAL CONFIGURATION FOR HIGH-PRECISION SCATTEROMETRIC MEASUREMENT

BACKGROUND OF THE INVENTION

1. Technical Field

The present disclosure relates to apparatus and methods for inspecting and analyzing semiconductor wafers and other substrates using scatterometry and related techniques.

2. Description of the Background Art

Scatterometry refers to an optical technique that analyzes diffracted light to deduce structural details of a diffracting sample. The diffracting sample is generally a periodic structure, that is, a "grating." Scatterometry may be used to measure or analyze two-dimensional structures (line gratings), as well as three-dimensional structures (such as periodic patterns of mesas or vias on a substrate).

FIG. 1A is a schematic view of a spectroscopic scatterometer system 10. As shown in FIG. 1A, system 10 may be used to measure reflected or transmitted intensities or changes in polarization states of the diffracted light. As shown in FIG. 1A, a semiconductor wafer 11 may comprise a silicon substrate 12, and a structure 16 thereon that may include a photoresist pattern on and/or over film stack(s), where the film(s) are at least partially light-transmissive and has a certain film thickness and refractive index (n and k, the real and imaginary components of the index).

An XYZ stage 14 is used for moving the wafer in the horizontal XY directions. Stage 14 may also be used to adjust the z height of the wafer 11. A broadband radiation source such as white light source 22 supplies light through a fiber optic cable 24 which randomizes the polarization and creates a uniform light source for illuminating the wafer. Preferably, source 22 supplies electromagnetic radiation having wavelengths in the range of at least 180 to 800 nm. Upon emerging from fiber 24, the radiation passes through an optical illuminator that may include an aperture and a focusing lens or mirror (not shown). The aperture causes the emerging light beam to image a small area of structure 16. The light emerging from illuminator 26 is polarized by a polarizer 28 to produce a polarized sampling beam 30 illuminating the structure 16.

The radiation originating from sampling beam 30 that is reflected by structure 16, passed through an analyzer 32 and to a spectroscopic ellipsometry (SE) spectrometer 34 to detect different spectral components of the reflected radiation, such as those in the spectrum of the radiation source 22, to obtain a signature of the structure. In one mode (spectrophotometry mode) of operation, the reflected intensities are then used in a manner described below to find the value(s) of one or more parameters of structure 16. The system 10 can also be modified by placing the spectrometer 34 on the side of structure 16 opposite to illumination beam 30 to measure the intensities of radiation transmitted through structure 16 instead for the same purpose. These reflected or transmitted intensity components are supplied to computer 40. Alternatively, the light reflected by the structure 16 is collected by lens 54, passes through the beam splitter 52 to a spectrometer 60. The spectral components at different wavelengths measured are detected and signals representing such components are supplied to computer 40. The light reflected by structure 16 may be supplied by source 22 through illuminator 26 as described above or through other optical components in another arrangement. Thus, in such arrangement, lens 23 collects and directs radiation from source 22 to a beam splitter 52, which reflects part of the incoming beam towards the focus lens 54 which focuses the radiation to structure 16. The light reflected by the structure 16 is collected by lens 54, passes through the beam splitter 52 to a spectrometer 60.

When the system 10 is operated in another mode (spectroscopic ellipsometry mode) used to measure the changes in polarization state caused by the diffraction by the structure, either the polarizer 28 or the analyzer 30 is rotated (to cause relative rotational motion between the polarizer and the analyzer) when spectrometer 34 is detecting the diffracted radiation from structure 16 at a plurality of wavelengths, such as those in the spectrum of the radiation source 22, where the rotation is controlled by computer 40 in a manner known to those skilled in the art. The diffracted intensities at different wavelengths detected are supplied to computer 40, which derives the changes in polarization state data at different wavelengths from the intensities in a manner known to those in the art.

FIG. 1B is a cross-sectional view of an example structure 16 on substrate 12, which structure comprises a diffracting structure 16b situated between the film stack 16a above the structure and the film stack 16c underneath the structure, and an incident electromagnetic beam 30 to illustrate operation of the spectroscopic scatterometer system 10. Thus, the incident beam 30 of the electromagnetic radiation first encounters the interface between the air and the film stack 16a and interfaces that may be present within the stack. Next, the portion of the radiation from beam 30 that penetrates the film stack 16a is diffracted by the grating structure 16b. At least some of the radiation from beam 30 will reach the film stack 16c underneath the grating and be reflected by or transmitted through interfaces associated with stack 16c. The total light reflectance is affected both by the grating and by the film stacks above and/or below the grating. Multi-layer interference, caused by multiple reflections between the films and the grating, creates a complicated pattern in a reflectance spectrum, which can be used for measuring parameters of the structure. A part of radiation from beam 30 that is not reflected or diffracted as described above will be transmitted into the substrate 12. As shown in FIG. 1B, the grating 16b has a height of H, a critical dimension CD and a side wall angle (SWA) as indicated.

SUMMARY

The present application discloses a method for selecting an optical configuration for a high-precision scatterometric measurement. A geometric parameterization of a grating is determined, wherein the grating comprises a periodic structure. The geometric parameterization is used to generate a representative set of model structures. An eigenvalue method is utilized to compute, for each model structure, a set of solutions which satisfy a Rayleigh condition within the grating. The Raleigh condition within the grating is satisfied when a vertical component of a propagating mode within the grating is zero.

Other embodiments, features and aspects are also disclosed herein.

DETAILED DESCRIPTION

Figure 1A:
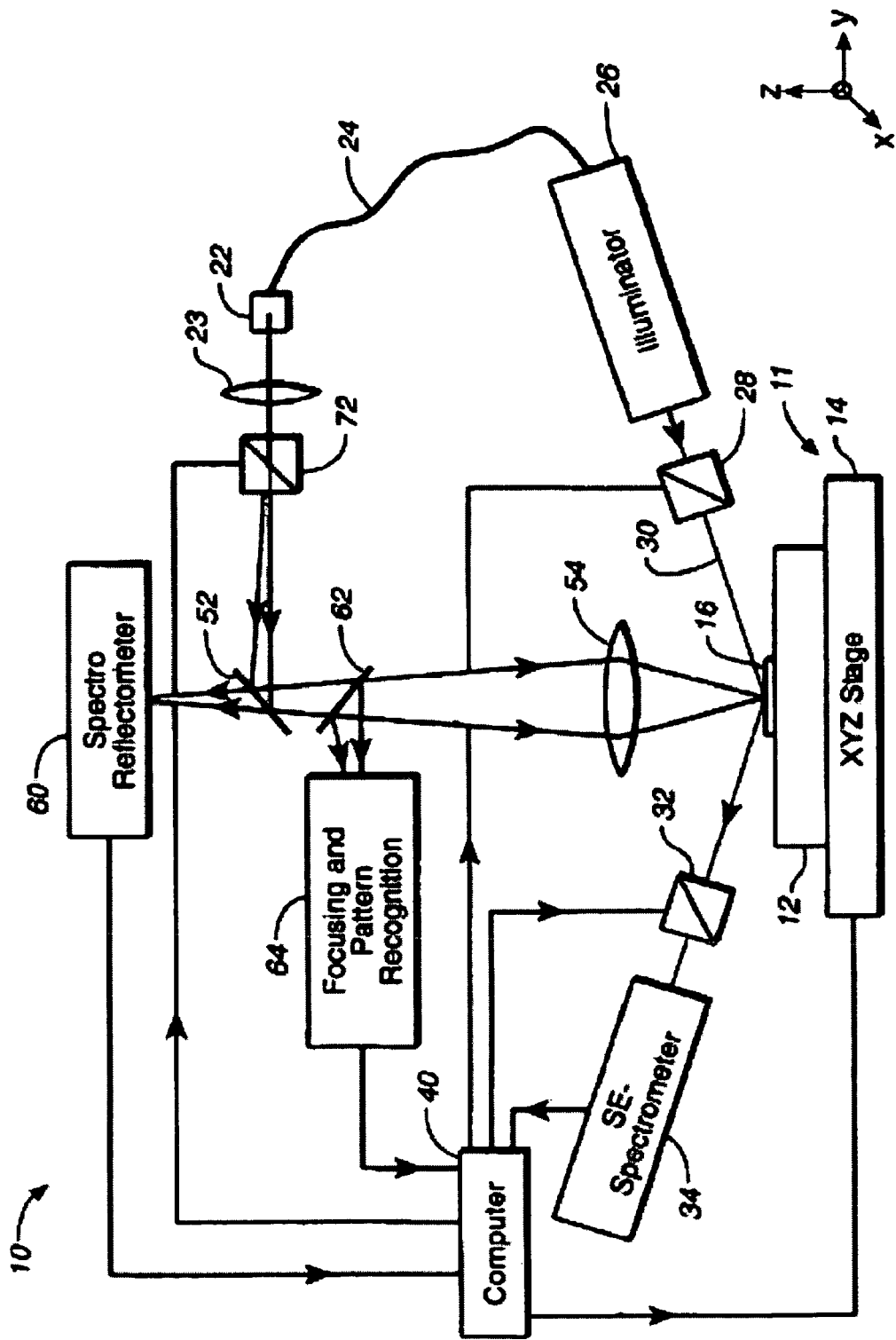
FIG. 1A is a schematic view of a spectroscopic scatterometer system.
Figure 1B:
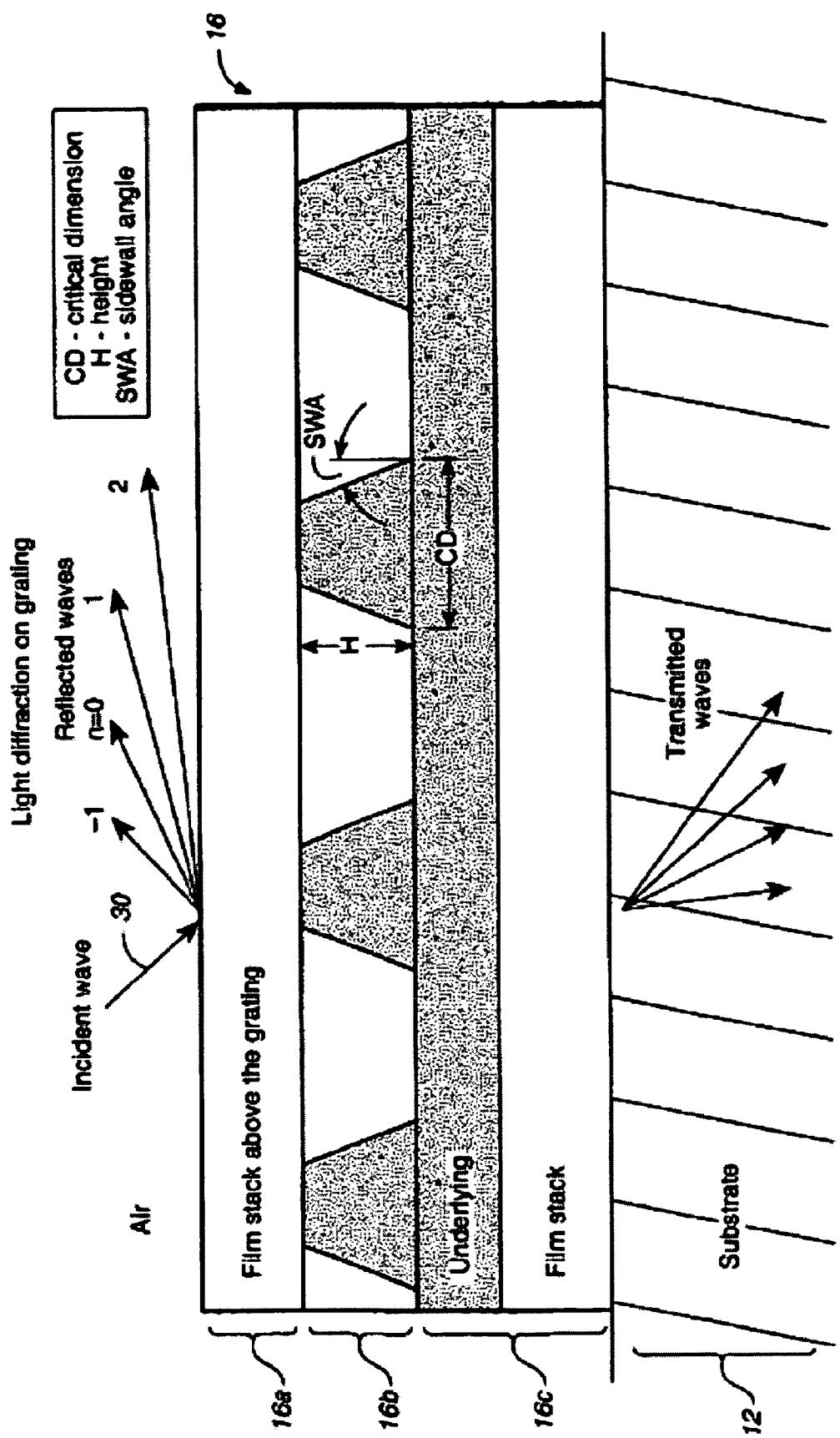
FIG. 1B is a cross-sectional view of an example structure on substrate and an incident electromagnetic beam to illustrate operation of the spectroscopic scatterometer system.

The setup of a scatterometry measurement system, such as the one described above, typically requires the user to determine and fix a multitude of measurement parameters. These parameters generally affect the tool configuration or the modeling calculation or both. Tool parameters may include a polar angle of incidence, an azimuth angle, and a numerical aperture. Modeling parameters may include the profile representation, wavelength set, and computation parameters. It is desirable to be able to pick an optimal configuration that maximizes sensitivity and precision, while minimizing noise, systematic errors and measurement time. The present application focuses on the identification of combinations of incidence angles, θ, and/or wavelengths, λ, where high parametric sensitivities in scatterometric measurements are expected given a specific periodic structure at a surface of a sample substrate (i.e. given a specific "grating").

One of the tasks required for making a precise measurement with an ellipsometric system is to identify the optical configuration that maximizes the information available from each measurement. In the case of an ellipsometer illuminating a grating that is classically mounted, a necessary condition for maximizing this information consists in finding a set of wavelengths and incidence angles that exhibit high sensitivity to the parametric description of the measured grating.

Previously, it has been noted that areas of parametric sensitivity in wavelength/incidence angle $\{\lambda,\theta\}$ space may be found near curves defined by the reflection Rayleigh manifold. The reflection Rayleigh manifold is the manifold in $\{\lambda,\theta\}$ space where the vertical component of the propagating mode in the space or air above the grating is zero. In the case of ellipsometric measurements, where the incidence angle is often fixed, this prior method identifies possible wavelengths at which to sample the spectra for optimal precision measurements. In other words, wavelengths were identified that are near the Rayleigh wavelengths in the "superstrate" for a given fixed incidence angle. (By "superstrate," we mean the media above the grating with the media typically being air.) In the case of a single wavelength reflectometer, the Rayleigh condition of interest is the set of angles for which the vertical component of the propagating mode in the space or air above the grating is zero.

Empirical studies have shown, however, that for many grating structures, there are other areas of high parametric sensitivity that are away from the reflection Rayleigh manifold. Moreover, the magnitude of the sensitivity in these other areas may be significantly higher than the area determined by the conventional technique using the reflection Rayleigh manifold.

The present application postulates and discloses a method novel Rayleigh manifold which is distinct from a conventional reflection (or transmission) Rayleigh manifold. While the conventional reflection Rayleigh manifold is based on k-vectors computed in the superstrate (typically, the air) above the grating, the new Rayleigh manifold disclosed herein is based on k-vectors computed within the grating itself. As such, this new Rayleigh manifold is termed herein as the "grating Rayleigh" manifold. For a fixed wavelength, the incidence angles that satisfy the Rayleigh condition in the grating are called "grating Rayleigh" angles.

Figure 2A:
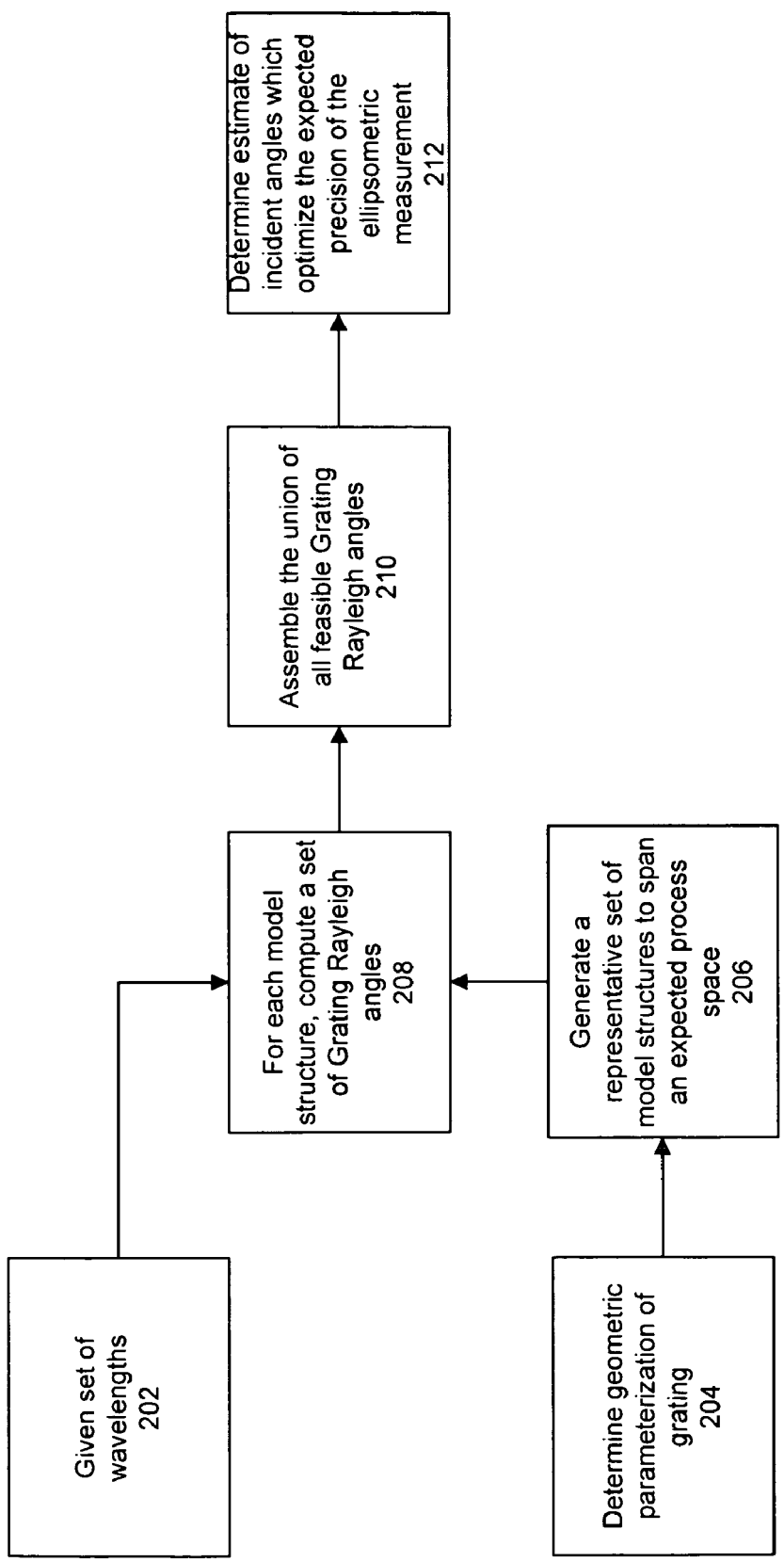
FIG. 2A is a flow chart depicting a method for selecting an optical configuration for a high-precision scatterometric measurement in accordance with an embodiment of the invention.

In accordance with an embodiment of the invention, given a set of fixed illuminating wavelengths, an optical configuration for a high-precision scatterometric measurement may be determined using the following steps. These steps are depicted in the method 200 shown in FIG. 2A. In this method, a set of incident wavelengths is given (or otherwise determined) 202 for a scatterometric measurement.

Regarding the grating structure being measured, a geometric parameterization is determined 204 for the grating. Using the geometric parameterization, a representative set of model structures are generated 206 to span an expected process space. In other words, one or more features and/or characteristics of the sample grating structure are expected to vary due to process variations. These features and/or characteristics are parameterized so as to be able to form model structures, and a set of model structures is created to cover the anticipated range of structures due to process variations.

In accordance with an embodiment of the invention, for each model structure in the representative set, a set of grating Rayleigh angles are computed 208. As described further herein, this computation may be performed, for example, by solving an associated or auxiliary eigenvalue problem. While solving the auxiliary eigenvalue problem is a more accurate method of approximating the grating Rayleigh manifold, an alternate method involves using an effective medium approximation of the grating to construct a fast estimate of the manifold, and thereby a set of Rayleigh angles.

Per block 210, the union of all of the sets of grating Rayleigh angles is plotted. From that plot, an estimate may be determined 212 of the incident angles which optimize the expected precision of the ellipsometric measurement.

Figure 2B:
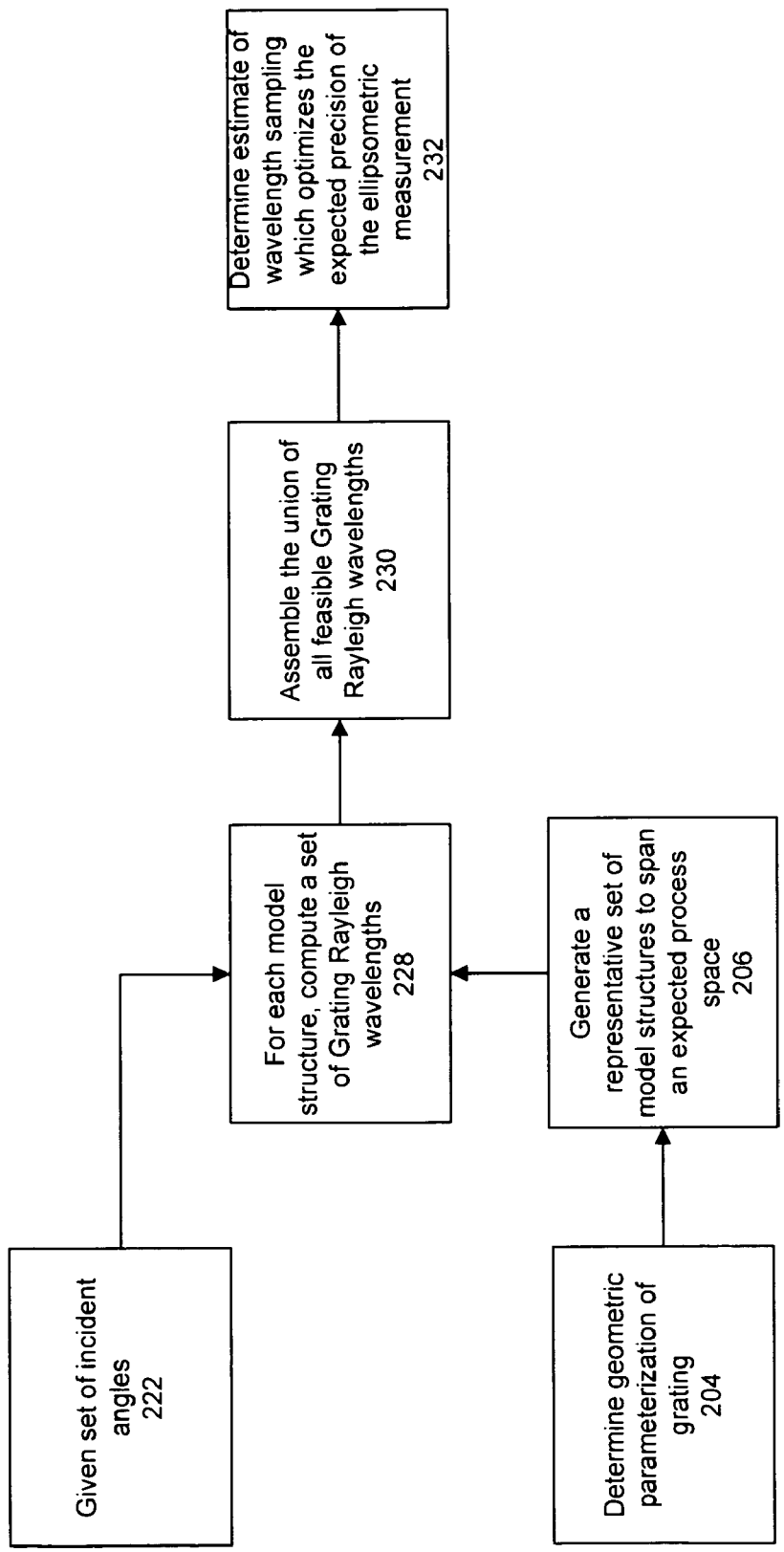
FIG. 2B is a flow chart depicting an alternate method for selecting an optical configuration for a high-precision scatterometric measurement in accordance with an embodiment of the invention.

An alternate method 250 is depicted in FIG. 2B. In this alternate method, a set of (polar) angles of incidence may be given 222. In this case, for each model, a set of Grating Rayleigh angles are computed 228, and the union of the Grating Rayleigh angles is plotted 230. An estimate of the wavelength sampling which optimizes the expected precision of the ellipsometric measurement is then determined 232.

Figure 3:
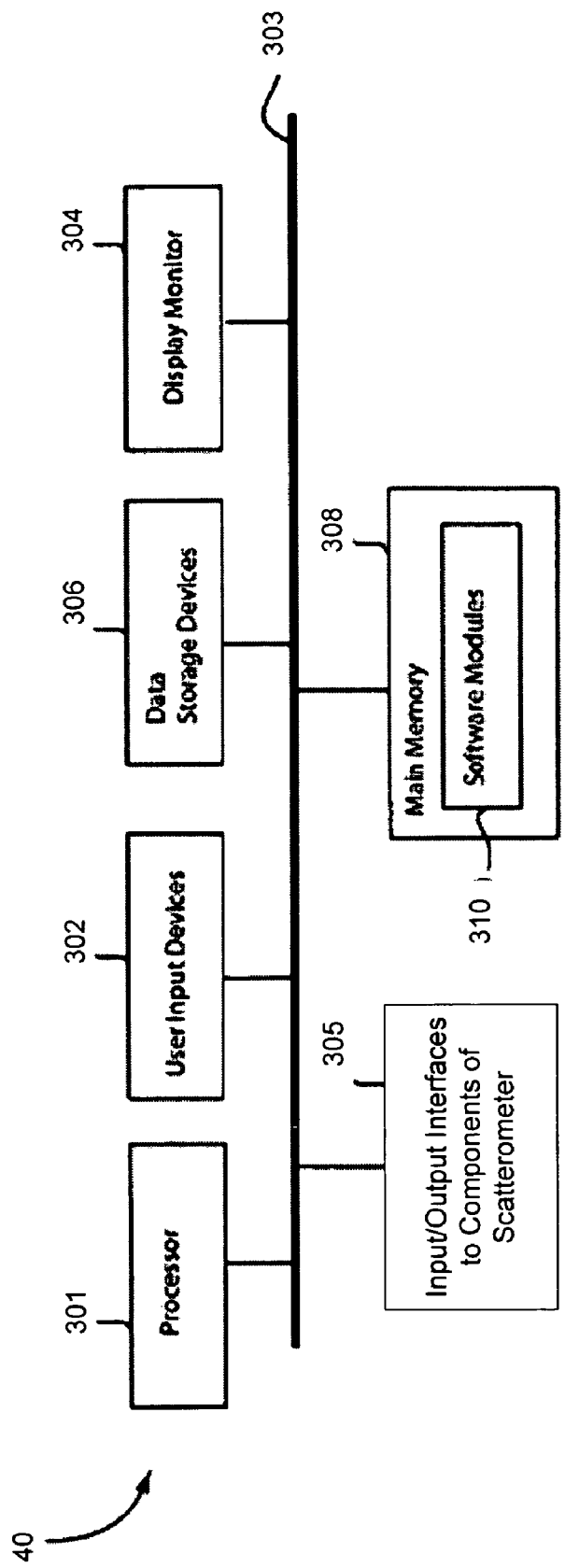
FIG. 3 is a schematic diagram of a computer apparatus in accordance with an embodiment of the invention.

FIG. 3 is a schematic diagram of an example computer system or apparatus 40 which may be used to control a scatterometer apparatus and for selecting an optical configuration for a high-precision scatterometric measurement in accordance with an embodiment of the invention. The computer 40 may have less or more components than illustrated. The computer 40 may include a processor 301, such as those from the Intel Corporation or Advanced Micro Devices, for example. The computer 40 may have one or more buses 303 coupling its various components. The computer 40 may include one or more user input devices 302 (e.g., keyboard, mouse), one or more data storage devices 306 (e.g., hard drive, optical disk, USB memory), a display monitor 304 (e.g., LCD, flat panel monitor, CRT), input/output interfaces 305 to scatterometer components, and a main memory 308 (e.g., RAM). Other components and capabilities may also be included. For example, multiple processors may be included.

In the example of FIG. 3, the main memory 308 includes software modules 310, which may be software components to perform the computer-implemented procedures and computations disclosed in this patent application. The software modules 310 may be loaded from the data storage device 306 to the main memory 308 for execution by the processor 301.

Reflection Rayleigh Manifolds

Previously, one method for finding a set of wavelengths and incidence angles that exhibit high sensitivity to the parametric description of a measured grating involved identifying wavelengths near the Rayleigh manifold in the superstrate. By superstrate, we mean the medium above the grating, that medium typically being air.

Suppose we have a grating with a defined pitch, and we direct monochromatic light at this grating at a given incidence and azimuth angle. Rayleigh manifolds are defined as those combinations of wavelength, incidence and azimuth angle when the component of the propagation in the vertical direction is zero.

The most common class of Rayleigh manifolds is that for which the incidence angle is fixed and the azimuth angle is zero (corresponding to the so-called classical grating mounting) and where the wavelength is allowed to vary. In this case, the manifold becomes points in wavelength space, hence the name Rayleigh wavelengths. These, as it happens may be computed in closed form.

First we define the horizontal component of the k-vector $$k_x = k_0 \left( N_I \sin\theta - m\frac{\lambda}{p} \right) \quad (1)$$

where $N_I$ is the index of refraction for the region above the grating, $\theta$ is the incidence angle, m is the diffraction order, $\lambda$ is the wavelength, $k_0 = 2\pi/\lambda$, and p is the pitch of the grating. The square of the vertical component of the k-vector is given as $$k_z^2 = N_I^2 k_0^2 - k_x^2 \quad (2)$$

Equating the above equation to zero and solving for $\lambda$ gives the Rayleigh wavelengths for a fixed incidence angle.

$$\lambda_R = \frac{N_I p}{m}(\sin\theta \pm 1) \quad (3)$$

Equivalently, we can solve for $\theta$, which gives the Rayleigh angles for a fixed illumination wavelength.

$$\theta_R = \sin^{-1}\left(\frac{m\lambda}{N_I p} \pm 1\right) \quad (4)$$

2D Grating Rayleigh Manifolds

We turn now to the question of a Rayleigh manifold in the grating region. In this case, consider a two-dimensional grating, and recall that, a two-dimensional grating refers to a line grating. In addition, consider a classical mounting configuration which has a fixed angle of incidence for an ellipsometer.

This analysis relies heavily on the notion that the grating structure may be divided into horizontal regions (slabs) where the permittivity is considered to be constant with respect to the vertical direction. The analogous condition is derived from the observation that if one uses an ordinary differential equation to define the evolution of the fields in the vertical direction, and that if the differential (state) operator has eigenvalue equal to zero, then for this eigenmode there can be propagation only in the horizontal direction. This problem may be further simplified by approximating the state operator by a matrix, as in the case of rigorous coupled-wave analysis (RCWA). See Formulation for a stable and efficient implementation of the rigorous coupled-wave analysis of binary gratings, Moharam, M. G., et al., *J Opt Soc. Am. A*, Vol. 12, No 5 May 1995, pp. 1068-1076.

First, let us examine the Rayleigh condition in a uniform slab whose material has a real valued index of refraction $N_S$. Furthermore, we presume a mathematical description of the slab given by RCWA, which namely ascribes a truncated Fourier series for the permittivity function in the horizontal direction (x). The fields are also described as a truncated Fourier series for the permittivity function in the horizontal direction and as a vector-valued second-order ordinary differential equation in the vertical direction (z). The state matrix for ordinary differential equation (ODE) in the transverse electric (TE) case is given by the equation $$C = K_x^2 - N_S^2 I \quad (5)$$

where $$[K_x]_{mn} = N_I \sin\theta - m\frac{\lambda}{p} \quad (6)$$

Since the state matrix C is diagonal, each elementary vector $e_i = [0, \ldots, 0, 1, 0, \ldots, 0]^T$ is an eigenvector of the system, and thus each diffraction order m will be decoupled from one another. In such a case, the Rayleigh condition is satisfied when $$N_I^2 \sin^2\theta - 2m\frac{\lambda}{p}N_I \sin\theta + \left(m^2\frac{\lambda^2}{p^2} - N_S^2\right) = 0 \quad (7)$$

This equation may be viewed both as a quadratic equation as a function of $\lambda$ or $\sin\theta$. For example, if one fixes the wavelength, the Rayleigh angle is $$\theta_R = \sin^{-1}\left(\frac{1}{N_I}\left(m\frac{\lambda}{p} \pm N_S\right)\right) \quad (8)$$

It is interesting to note, that for $N_S = N_I$, the above result is identical to that which describes the Rayleigh manifolds in the superstrate.

If the slab is not modeled homogeneous material, the problem becomes somewhat more complicated. One solution is to follow that of the outline above, but replace $N_s$ by the mean index of refraction for the slab. For example, if the slab contains two materials with index of refraction $N_A$ and $N_B$ and their relative widths are ¼ and ¾ of the pitch then the effective media approximation will give a mean index of refraction of $N_s = \frac{1}{4}N_A + \frac{3}{4}N_B$. Note that because this relationship presumes a fixed index of refraction as a function of wavelengths, which is not the case for dispersive materials, the usefulness of this approach is limited to computing angles for which the Rayleigh condition holds. If, however, an analytic model of the index of refraction as a function of wavelength may be produced, then a Newton step type algorithm may be used to find the zeros of the function given in (7).

To compute this quantity more accurately, we return to the State Matrix in the ODE for the TE diffraction mode of a classically mounted grating. In this case, it is written as $$C = K_x^2 - E \qquad (10)$$

$$= (N_I^2 \sin^2\theta)I - \left(2N_I \frac{\lambda}{p}\sin\theta\right)D + \frac{\lambda^2}{p^2}D^2 - E$$

where D=diag ([$-n_f$, ..., $-1$, $0$, $1$, ..., $n_f$]), and $n_f$ is the maximum Fourier order in the expansion of the horizontal transverse electric field, and where E is the Toeplitz matrix formed from the Fourier coefficients from the Fourier expansion of the permittivity function in the horizontal direction.

Suppose we have fixed the wavelength and wish to find the value of $\theta$ such that an eigenvalue of the matrix C is equal to zero. To do this, we first examine the auxiliary matrix $$R = \begin{bmatrix} 0 & I \\ \frac{1}{N_I^2}\left(E - \left(\frac{\lambda}{p}\right)^2 D^2\right) & \left(\frac{2\lambda}{N_I p}\right)D \end{bmatrix} \qquad (11)$$

The eigenvalues of this equation satisfy the equation $$|R - sI| = 0 \qquad (12)$$

or $$\begin{vmatrix} -sI & I \\ \frac{1}{N_I^2}\left(E - \left(\frac{\lambda}{p}\right)^2 D^2\right) & \left(\frac{2\lambda}{N_I p}\right)D - sI \end{vmatrix} = 0 \qquad (13)$$

By examining the Schur complements in the equation above, we note that the characteristic polynomial of R may be equivalently expressed $$\left| s^2 I - s\left(\frac{2\lambda}{N_I p}\right)D - \frac{1}{N_I^2}\left(E - \left(\frac{\lambda}{p}\right)^2 D^2\right) \right| = 0 \qquad (14)$$

Noting the similarities between (10) and (14), we assert that if Q is the set of eigenvalues of R, the candidate set of Rayleigh angles may be computed as $$\Theta = \sin^{-1}(Q) \qquad (15)$$

The values in Q will generally not all be within the domain for which the angle $\theta$ is physically realizable, leading, for example, to candidate angles which are complex. These are to be discarded, with those positive real angles between 0 and $$\frac{\pi}{2}$$

being retained as desirable angles for configuring the optical instrument.

Conical Mountings

In the example above, we presumed that the azimuth angle of the incident light was zero, corresponding to the light impinging perpendicularly upon the grating. This illumination geometry is referred to as the classical mounting. This raises the question of how to identify the grating Rayleigh condition in those cases where the incident angles are not zero, corresponding to the conical mounting.

In order to analyze this problem, we return to RCWA. For the classical mounting, the state matrix, H, is a product of matrices FG, where $$H = FG \qquad (16)$$

$$F = \begin{bmatrix} -K_x K_y & K_x^2 - E \\ A^{-1} - K_y^2 & K_y K_x \end{bmatrix}$$

$$G = \begin{bmatrix} -K_x E^{-1} K_y & K_x E^{-1} K_x - I \\ I - K_y E^{-1} K_y & K_y E^{-1} K_x \end{bmatrix}$$

where the matrix E is defined as before, where the matrix A is the Toeplitz matrix formed by the Fourier coefficients from the Fourier expansion of the inverse permittivity function in the horizontal direction. The definition of $K_x$ is slightly modified in the conical mounting case, with $$K_x = N_I \cos\phi\sin\theta - \frac{\lambda}{p}D \qquad (17)$$

$$K_y = N_I \sin\phi\sin\theta$$

As with the classical mounting problem we will proceed by setting the azimuth angle to a given value, and identifying feasible values of the incidence angle by examining the eigenvalues of an auxiliary matrix. As before, we will find those values of the incidence angle for which an eigenvalue of the state matrix, in this case H, is zero. At first glance, the problem seems significantly more complicated, as the state matrix H is composed as a product of matrices. Fortunately, we will be able to take advantage of the following property, namely, that the matrix product FG will have a zero eigenvalue if either F or G has a zero eigenvalue. Thus, we will be concerned with finding the conditions such that the eigenvalues of F will be zero.

Rewriting the matrix F in terms of the diagonal matrix D (previously defined) we have:

$$F = \sin^2\theta M_2 + \sin\theta M_1 + M_0 \qquad (18)$$

where $$M_2 = N_I^2 \begin{bmatrix} -\cos\phi\sin\phi I & \cos^2\phi I \\ -\sin^2\phi I & \cos\phi\sin\phi I \end{bmatrix} \qquad (19)$$

$$M_1 = N_I \frac{\lambda}{p} \begin{bmatrix} \sin\phi D & -2\cos\phi D \\ 0 & -\sin\phi D \end{bmatrix}$$

$$M_0 = \begin{bmatrix} 0 & \frac{\lambda^2}{p^2}D^2 - E \\ A^{-1} & 0 \end{bmatrix}$$

As before, we examine eigenvalues of the auxiliary matrix S where $$S = \begin{bmatrix} 0 & I \\ -M_2^{-1}M_0 & -M_2^{-1}M_1 \end{bmatrix} \quad (20)$$

The eigenvalues of this equation satisfy the equation $$|S - sI| = 0 \quad (21)$$

or $$\begin{vmatrix} -sI & I \\ -M_2^{-1}M_0 & -M_2^{-1}M_1 - sI \end{vmatrix} = 0 \quad (22)$$

By examining the Schur complements in the equation above, we note that the characteristic polynomial of S may be equivalently expressed $$|s^2 M_2 + s M_1 + M_0| = 0 \quad (23)$$

Noting the similarities between (18) and (23), we assert that if Q is the set of eigenvalues of S, the candidate set of Rayleigh angles may be computed as in (15).

As before, the values in Q will generally not all be within the domain for which the angle θ is physically realizable, leading, for example, to candidate angles which are complex. These are to be discarded, with those positive real angles between 0 and $$\frac{\pi}{2}$$

being retained as desirable angles for configuring the optical instrument. By repeating procedure of identifying feasible values of the incidence angle θ for a sufficiently dense set of the azimuth angle φ, we have a set of order pairs {θ,φ} for which the grating Rayleigh condition holds.

CONCLUSION

In conclusion, the optical configuration determination technique disclosed herein provides a highly inventive way to determine regions (in parameter space) of high parametric sensitivity that are not found at the manifold in {λ,θ} space associated with reflection (or transmission) Rayleigh manifolds. Rather, these regions of high parametric sensitivity occur at so-called "grating Rayleigh" manifolds which are defined and disclosed in the present patent application.

Advantageously, applicant believes that there is a likelihood of more precise scatterometric measurements when spectra are sampled in {λ,θ} space near a Grating Rayleigh Manifold, than when spectra are sampled in {λ,θ} space near a Reflection or transmission Rayleigh manifold. This is because Reflection and transmission Rayleigh manifolds are independent of the geometric parameterization of the grating, except for pitch. In contrast, a Grating Rayleigh Manifold is highly dependent on the geometric parameterization of the grating, which makes precise measurements more likely to be achieved.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method for selecting and using an optical configuration for a high-precision scatterometric measurement, the method comprising:
   a computer apparatus determining a geometric parameterization of a grating, wherein the grating comprises a periodic structure;
   the computer apparatus using the geometric parameterization to generate a representative set of model structures;
   the computer apparatus utilizing a computational method to identify, for each model structure, a set of solutions which satisfy a Rayleigh condition within the grating; and
   a scatterometry apparatus performing the scatterometric measurement on a target substrate with incident angles determined using said set of solutions from the computer apparatus.

2. The method of claim 1, wherein the Raleigh condition within the grating is satisfied when a vertical component of a propagating mode within the grating is zero.

3. The method of claim 2, wherein a k-vector corresponds to the propagating mode, and wherein $k_z^2 = N_I^2 k_0^2 - k_x^2$, where $k_z$ is the vertical component of the k-vector, $N_I$ is an index of refraction for a region above the grating, $k_0 = 2\pi/\lambda$, λ is a wavelength for the scatterometric measurement, and $k_x$ is a horizontal component of the k-vector.

4. The method of claim 3, wherein the grating is approximated by film with an effective medium with an index of refraction of $N_S$.

5. The method of claim 4, wherein a candidate set of grating Rayleigh incidence angles, $\theta_R$, comprises $$\theta_R = \sin^{-1}\left(\frac{1}{N_I}\left(m\frac{\lambda}{p} \pm N_S\right)\right)$$

where p is a pitch of the grating, λ is chosen from a set of illuminating wavelengths, and m is an integer variable representing diffraction order.

6. The method of claim 4, wherein a candidate set of grating Rayleigh wavelengths are approximated by computing the zeros (in λ) of the function $$N_I^2 \sin^2\theta - 2m\frac{\lambda}{p} N_I \sin\theta + \left(m^2\frac{\lambda^2}{p^2} - N_S^2\right).$$

where p is a pitch of the grating, $\lambda$ is chosen from a set of illuminating wavelengths, and m is an integer variable representing diffraction order.

7. The method of claim 6, where the effective media approximation, $N_S$, is a linear or nonlinear function of wavelength.

8. The method of claim 2, wherein a candidate set of grating Rayleigh incidence angles is computed by computing eigenvalues of an auxiliary matrix related to state matrices from a Maxwell's equation solver based on Fourier expansion of electromagnetic fields.

9. The method of claim 8, wherein the Maxwell's equation solver uses rigorous coupled-wave analysis (RCWA).

10. The method of claim 9, wherein the auxiliary matrix is given by $$R = \begin{bmatrix} 0 & I \\ \frac{1}{N_I^2}\left(E - \left(\frac{\lambda}{p}\right)^2 D^2\right) & \frac{2\lambda}{N_I p}D \end{bmatrix}$$

where $N_I$ is an index of refraction for a superstrate, E is a Toeplitz matrix whose elements consist of Fourier components of a horizontally varying permittivity function, p is a pitch of the grating, $\lambda$ is chosen from a set of illuminating wavelengths, and where D is a diagonal index matrix.

11. An apparatus for model-based scatterometric measurement of semiconductor device features on a substrate, the apparatus comprising:
    a scatterometer tool for performing diffraction measurements on the substrate; and
    a data processing system configured to perform computations for selecting an optical configuration for a high-precision scatterometric measurement,
    wherein the data processing system is further configured to (i) determine a geometric parameterization of a grating, wherein the grating comprises a periodic structure, (ii) use the geometric parameterization to generate a representative set of model structures, and (iii) utilize a computational model to identify, for each model structure, a set of solutions which satisfy a Rayleigh condition within the grating.

12. The apparatus of claim 11, wherein the Raleigh condition within the grating is satisfied when a vertical component of a propagating mode within the grating is zero.

13. The apparatus of claim 12, wherein a k-vector corresponds to the propagating mode, and wherein $k_z^2 = N_I^2 k_0^2 - k_x^2$, where $k_z$ is the vertical component of the k-vector, $N_I$ is an index of refraction for a region above the grating, $k_0 = 2\pi/\lambda$, $\lambda$ is a wavelength for the scatterometric measurement, and $k_x$ is a horizontal component of the k-vector.

14. The apparatus of claim 13, wherein the grating is approximated by film with an effective medium with an index of refraction of $N_S$.

15. The apparatus of claim 14, wherein a candidate set of grating Rayleigh incidence angles, $\theta_R$, comprises $$\theta_R = \sin^{-1}\left(\frac{1}{N_I}\left(m\frac{\lambda}{p} \pm N_S\right)\right)$$

where p is a pitch of the grating, $\lambda$ is chosen from a set of illuminating wavelengths, and m is an integer variable representing diffraction order.

16. The apparatus of claim 14, wherein a candidate set of grating Rayleigh wavelengths are approximated by computing the zeros (in $\lambda$) of the function $$N_I^2 \sin^2\theta - 2m\frac{\lambda}{p}N_I \sin\theta + \left(m^2\frac{\lambda^2}{p^2} - N_S^2\right),$$

where p is a pitch of the grating, $\lambda$ is chosen from a set of illuminating wavelengths, and m is an integer variable representing diffraction order.

17. The apparatus of claim 16, where the effective media approximation, $N_S$, is a linear or nonlinear function of wavelength.

18. The apparatus of claim 12, wherein a candidate set of grating Rayleigh incidence angles is computed by computing eigenvalues of an auxiliary matrix related to state matrices from a Maxwell's equation solver based on Fourier expansion of electromagnetic fields.

19. The apparatus of claim 18, wherein the Maxwell's equation solver comprises a rigorous coupled-wave analysis (RCWA) solver.

20. The apparatus of claim 19, where the RCWA solver is that for a Transverse Electric mode for a classically mounted grating.

21. The apparatus of claim 20, wherein the auxiliary matrix is given by $$R = \begin{bmatrix} 0 & I \\ \frac{1}{N_I^2}\left(E - \left(\frac{\lambda}{p}\right)^2 D^2\right) & \frac{2\lambda}{N_I p}D \end{bmatrix}$$

where $N_I$ is an index of refraction for a superstrate, E is a Toeplitz matrix whose elements consist of Fourier components of a horizontally varying permittivity function, p is a pitch of the grating, $\lambda$ is chosen from a set of illuminating wavelengths, and where D is a diagonal index matrix.

22. The apparatus of claim 19, where the RCWA solver is that for coupled Transverse Electric and Magnetic modes for a conically mounted grating.

23. The apparatus of claim 22, wherein the auxiliary matrix is given by $$S = \begin{bmatrix} 0 & I \\ -M_2^{-1}M_0 & -M_2^{-1}M_1 \end{bmatrix} \text{ where } M_2 = N_I^2 \begin{bmatrix} -\cos\phi\sin\phi I & \cos^2\phi I \\ -\sin^2\phi I & \cos\phi\sin\phi I \end{bmatrix},$$

$$M_1 = N_I\frac{\lambda}{p}\begin{bmatrix} \sin\phi D & -2\cos\phi D \\ 0 & -\sin\phi D \end{bmatrix}, M_0 = \begin{bmatrix} 0 & \frac{\lambda^2}{p^2}D^2 - E \\ A^{-1} & 0 \end{bmatrix},$$

$N_I$ is an index of refraction for a superstrate, E is a Toeplitz matrix whose elements consist of Fourier components of a horizontally varying permittivity function, A is a Toeplitz matrix whose elements consist of Fourier components of a horizontally varying inverse permittivity function, p is a pitch of the grating, $\lambda$ is chosen from a set of illuminating wavelengths, $\phi$ is chosen from a set of the azimuth angles of illumination, and where D is a diagonal index matrix.

24. A data storage medium storing computer-readable instructions for selecting an optical configuration for a high-precision scatterometric measurement, the data storage medium comprising:
- computer-readable instructions stored on the medium and configured to determine a geometric parameterization of a grating, wherein the grating comprises a periodic structure;
- computer-readable instructions stored on the medium and configured to use the geometric parameterization to generate a representative set of model structures; and
- computer-readable instructions stored on the medium and configured to utilize a computational method to identify, for each model structure, a set of solutions which satisfy a Rayleigh condition within the grating; and
- computer-readable instructions stored on the medium and configured to control a scatterometric apparatus so as to perform the scatterometric measurement on a target substrate with incident angles determined using said set of solutions.

* * * * *